(12) United States Patent
Eggen et al.

(10) Patent No.: US 8,295,943 B2
(45) Date of Patent: Oct. 23, 2012

(54) IMPLANTABLE MEDICAL LEAD WITH BIASED ELECTRODE

(75) Inventors: Michael D. Eggen, Lake Elmo, MN (US); John L. Sommer, Coon Rapids, MN (US); Michael Ebert, Fridley, MN (US); David Wayne Bourn, Maple Grove, MN (US); Gabriela C. Miyazawa, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 867 days.

(21) Appl. No.: 12/195,287

(22) Filed: Aug. 20, 2008

(65) Prior Publication Data
US 2009/0054936 A1 Feb. 26, 2009

Related U.S. Application Data

(60) Provisional application No. 61/049,226, filed on Apr. 30, 2008, provisional application No. 60/956,868, filed on Aug. 20, 2007, provisional application No. 60/956,832, filed on Aug. 20, 2007.

(51) Int. Cl.
*A61N 1/05* (2006.01)

(52) U.S. Cl. .......... 607/116; 607/119; 607/122

(58) Field of Classification Search .......... 607/115–119, 607/122
See application file for complete search history.

(56) References Cited

U.S. PATENT DOCUMENTS

| | | |
|---|---|---|
| 3,757,792 A | 9/1973 | Muller et al. |
| 4,106,512 A | 8/1978 | Bisping |
| 4,217,913 A | 8/1980 | Dutcher |
| 4,390,023 A | 6/1983 | Rise |
| 4,660,571 A | 4/1987 | Hess et al. |
| 4,662,382 A | 5/1987 | Sluetz et al. |
| 4,711,251 A | 12/1987 | Stokes |
| 4,819,647 A * | 4/1989 | Byers et al. ............ 607/116 |
| 4,922,607 A | 5/1990 | Doan et al. |
| 4,946,457 A | 8/1990 | Elliott |
| 4,961,434 A | 10/1990 | Stypulkowski |
| 5,000,194 A | 3/1991 | van den Honert et al. |
| 5,029,585 A | 7/1991 | Lieber et al. |
| 5,037,497 A | 8/1991 | Stypulkowski |

(Continued)

FOREIGN PATENT DOCUMENTS

EP  0 769 308 A1  4/1997

(Continued)

OTHER PUBLICATIONS

U.S. Appl. No. 12/195,277, filed Aug. 20, 2008, entitled Electrode Configurations for Directional Leads by Bourn et al.

(Continued)

*Primary Examiner* — Niketa I. Patel
*Assistant Examiner* — Joseph Stoklosa
(74) *Attorney, Agent, or Firm* — Reed A. Duthler (57) ABSTRACT

This disclosure describes implantable medical leads that include a lead body and an electrode. A width of the electrode as measured along a longitudinal direction of the lead varies about the perimeter of the lead. The uneven width of the electrode may bias a stimulation field in a particular direction, e.g., a radial or transverse direction relative to the longitudinal axis of the lead. Electrodes with an uneven width may be useful for controlling the direction of propagation of the stimulation field in order to, for example, avoid phrenic nerve stimulation during LV pacing or neck muscle stimulation during vagal neurostimulation.

13 Claims, 6 Drawing Sheets

U.S. PATENT DOCUMENTS

| | | | |
|---|---|---|---|
| 5,117,824 A | 6/1992 | Keimel et al. | |
| 5,246,014 A | 9/1993 | Williams et al. | |
| 5,324,310 A | 6/1994 | Greeninger et al. | |
| 5,431,693 A | 7/1995 | Schroeppel | |
| 5,462,545 A * | 10/1995 | Wang et al. | 606/41 |
| 5,522,874 A | 6/1996 | Gates | |
| 5,531,779 A | 7/1996 | Dahl et al. | |
| 5,534,018 A | 7/1996 | Wahlstrand et al. | |
| 5,584,873 A | 12/1996 | Shoberg et al. | |
| 5,601,615 A | 2/1997 | Markowitz et al. | |
| 5,643,330 A | 7/1997 | Holsheimer et al. | |
| 5,662,699 A | 9/1997 | Hamedi et al. | |
| 5,683,431 A | 11/1997 | Wang | |
| 5,741,214 A | 4/1998 | Ouchi et al. | |
| 5,755,664 A | 5/1998 | Rubenstein | |
| 5,755,766 A | 5/1998 | Chastain et al. | |
| 5,772,108 A | 6/1998 | Ruggiere, Sr. et al. | |
| 5,775,331 A | 7/1998 | Raymond et al. | |
| 5,800,465 A | 9/1998 | Thompson et al. | |
| 5,824,030 A | 10/1998 | Yang et al. | |
| 5,836,875 A | 11/1998 | Webster, Jr. | |
| 5,843,148 A | 12/1998 | Gijsbers et al. | |
| 5,861,012 A | 1/1999 | Stroebel | |
| 5,895,416 A | 4/1999 | Barreras, Sr. et al. | |
| 5,916,158 A | 6/1999 | Webster, Jr. | |
| 5,941,906 A | 8/1999 | Barreras, Sr. et al. | |
| 5,983,126 A | 11/1999 | Wittkampf | |
| 5,987,746 A | 11/1999 | Williams | |
| 6,052,624 A | 4/2000 | Mann | |
| 6,064,905 A | 5/2000 | Webster, Jr. et al. | |
| 6,071,279 A | 6/2000 | Whayne et al. | |
| 6,078,830 A | 6/2000 | Levine et al. | |
| 6,085,118 A | 7/2000 | Hirschberg et al. | |
| 6,146,379 A | 11/2000 | Fleischman et al. | |
| 6,161,029 A | 12/2000 | Spreigl et al. | |
| 6,205,360 B1 | 3/2001 | Carter et al. | |
| 6,263,250 B1 | 7/2001 | Skinner | |
| 6,317,633 B1 | 11/2001 | Jorgenson et al. | |
| 6,381,496 B1 | 4/2002 | Meadows et al. | |
| 6,393,325 B1 | 5/2002 | Mann et al. | |
| 6,430,425 B1 * | 8/2002 | Bisping | 600/374 |
| 6,510,347 B2 | 1/2003 | Borkan | |
| 6,609,032 B1 | 8/2003 | Woods et al. | |
| 6,643,546 B2 | 11/2003 | Mathis et al. | |
| 6,740,082 B2 * | 5/2004 | Shadduck | 606/41 |
| 6,839,588 B1 * | 1/2005 | Rudy | 600/523 |
| 6,978,178 B2 | 12/2005 | Sommer et al. | |
| 6,999,819 B2 | 2/2006 | Swoyer et al. | |
| 7,047,084 B2 | 5/2006 | Erickson et al. | |
| 7,162,299 B1 | 1/2007 | Kroll et al. | |
| 7,214,189 B2 | 5/2007 | Zdeblick | |
| 7,269,457 B2 | 9/2007 | Shafer et al. | |
| 7,295,875 B2 | 11/2007 | Wallace et al. | |
| 7,366,573 B2 | 4/2008 | Knapp et al. | |
| 2002/0183817 A1 | 12/2002 | Van Venrooij et al. | |
| 2002/0193834 A1 | 12/2002 | Levine | |
| 2003/0065365 A1 | 4/2003 | Zhu et al. | |
| 2003/0078623 A1 | 4/2003 | Weinberg et al. | |
| 2003/0083724 A1 | 5/2003 | Jog et al. | |
| 2003/0204232 A1 | 10/2003 | Sommer et al. | |
| 2003/0220676 A1 | 11/2003 | Helland | |
| 2003/0236558 A1 | 12/2003 | Whitehurst et al. | |
| 2004/0034394 A1 | 2/2004 | Woods et al. | |
| 2004/0088015 A1 | 5/2004 | Casavant et al. | |
| 2004/0098074 A1 | 5/2004 | Erickson et al. | |
| 2004/0167583 A1 | 8/2004 | Knudson et al. | |
| 2004/0172088 A1 | 9/2004 | Knudson et al. | |
| 2004/0193021 A1 | 9/2004 | Zdeblick et al. | |
| 2004/0193240 A1 | 9/2004 | Michel | |
| 2004/0260310 A1 | 12/2004 | Harris | |
| 2004/0267328 A1 | 12/2004 | Duffin et al. | |
| 2005/0038481 A1 | 2/2005 | Chinchoy et al. | |
| 2005/0038489 A1 * | 2/2005 | Grill | 607/116 |
| 2005/0131486 A1 | 6/2005 | Boveja et al. | |
| 2005/0131506 A1 | 6/2005 | Rezai et al. | |
| 2005/0137644 A1 | 6/2005 | Boveja et al. | |
| 2005/0143787 A1 | 6/2005 | Boveja et al. | |
| 2005/0171587 A1 | 8/2005 | Daglow et al. | |
| 2006/0058588 A1 * | 3/2006 | Zdeblick | 600/300 |
| 2006/0168805 A1 | 8/2006 | Hegland et al. | |
| 2006/0173262 A1 | 8/2006 | Hegland et al. | |
| 2006/0206158 A1 | 9/2006 | Wu et al. | |
| 2006/0241711 A1 | 10/2006 | Sathaye | |
| 2006/0247688 A1 | 11/2006 | Olson et al. | |
| 2007/0055124 A1 | 3/2007 | Viswanathan et al. | |
| 2007/0112402 A1 | 5/2007 | Grill et al. | |
| 2007/0135846 A1 | 6/2007 | Knudson et al. | |
| 2007/0135856 A1 | 6/2007 | knudson et al. | |
| 2007/0135857 A1 | 6/2007 | Knudson et al. | |
| 2007/0135858 A1 | 6/2007 | Knudson et al. | |
| 2007/0142870 A1 | 6/2007 | Knudson et al. | |
| 2007/0179579 A1 | 8/2007 | Feler et al. | |
| 2007/0203537 A1 | 8/2007 | Goetz et al. | |
| 2007/0203540 A1 | 8/2007 | Goetz et al. | |
| 2007/0203541 A1 | 8/2007 | Goetz et al. | |
| 2007/0203542 A1 | 8/2007 | Goetz et al. | |
| 2007/0203544 A1 | 8/2007 | Goetz et al. | |
| 2007/0203546 A1 * | 8/2007 | Stone et al. | 607/59 |
| 2008/0077186 A1 | 3/2008 | Thompson et al. | |
| 2008/0097566 A1 | 4/2008 | Colliou | |
| 2008/0255647 A1 | 10/2008 | Jensen et al. | |

FOREIGN PATENT DOCUMENTS

| | | |
|---|---|---|
| EP | 1 127 587 A2 | 8/2001 |
| EP | 1 438 984 A2 | 7/2004 |
| WO | WO 01/03767 | 1/2001 |
| WO | WO 01/74441 | 10/2001 |
| WO | WO 02/068042 | 9/2002 |
| WO | WO 2006/029090 | 3/2006 |
| WO | WO 2006/042039 | 4/2006 |
| WO | WO 2006/069322 | 6/2006 |
| WO | WO 2006/069323 | 6/2006 |
| WO | WO 2008/094879 | 8/2008 |

OTHER PUBLICATIONS

U.S. Appl. No. 12/195,317, filed Aug. 20, 2008, entitled Evaluating Therapeutic Stimulation Electrode Configurations Based on Physiological Responses by Sommer et al.

U.S. Appl. No. 12/195,313, filed Aug. 20, 2008, entitled Stimulation Filed Management by Eggen et al.

Notification of Transmittal of the International Search Report and the Written Opinion of the International Searching Authority, or the Declaration dated Dec. 12, 2008 for corresponding PCT Application No. PCT/US2008/009914 (12 pgs.).

International Report on Patentability from international application No. PCT/US2008/009914, dated Feb. 24, 2010, 7 pp.

Office Action from U.S. Appl. No. 12/195,313, dated Jan. 25, 2011, 6 pp.

Office Action from U.S. Appl. No. 12/195,277, dated Mar. 14, 2011, 17 pp.

* cited by examiner

IMPLANTABLE MEDICAL LEAD WITH BIASED ELECTRODE

This application claims the benefit of U.S. Provisional Application No. 60/956,832, filed Aug. 20, 2007, U.S. Provisional Application No. 60/956,868, filed Aug. 20, 2007 and U.S. Provisional Application No. 61/049,226, filed Apr. 30, 2008, each of which are hereby incorporated by reference.

TECHNICAL FIELD

The present disclosure relates to medical devices, more particularly to implantable medical leads.

BACKGROUND

In the medical field, implantable leads are used with a wide variety of medical devices. For example, implantable leads are used with implantable cardiac pacemakers that provide therapeutic stimulation to the heart by delivering pacing, cardioversion or defibrillation pulses via the leads. Implantable cardiac pacemakers deliver such pulses via electrodes disposed on the leads, e.g., near distal ends of the leads. Implantable medical leads may be configured to allow electrodes to be positioned at desired cardiac locations so that the pacemaker can deliver pulses to the desired locations.

Implantable medical leads are also used with other types of stimulators to provide, as examples, neurostimulation, muscular stimulation, or gastric stimulation to target patient tissue locations via electrodes on the leads and located within or proximate to the target tissue. As one example, implantable medical leads may be positioned proximate to the vagal nerve for delivery of neurostimulation to the vagal nerve. Additionally, implantable medical leads may be used by medical devices for patient sensing and, in some cases, for both sensing and stimulation. For example, electrodes on implantable medical leads may detect electrical signals within a patient, such as an electrocardiogram, in addition to delivering electrical stimulation.

For delivery of cardiac pacing pulses to the left ventricle (LV), an implantable medical lead is typically placed through the coronary sinus and into a coronary vein. However, when located in the coronary sinus or a coronary vein, an LV lead may also be located near the phrenic nerve. Phrenic nerve stimulation is generally undesirable during LV pacing therapy. In some instances, the implantable lead may need to be specifically positioned to avoid phrenic nerve stimulation during LV pacing therapy, which may result in placing the electrodes of the LV lead at a non-optimal site for LV pacing.

In some cases, implantable medical leads with ring electrodes are used as an alternative to cuff electrodes for delivery of neurostimulation to the vagal nerve. However, when located near the vagal nerve, the implantable medical lead may also be located near neck muscles. Stimulation of neck muscles is generally undesirable during therapeutic vagal stimulation.

SUMMARY OF THE DISCLOSURE

In general, the present disclosure is directed toward controlling the direction of a stimulation field. An implantable medical lead may include at least one ring or ring-like electrode with an uneven width. For example, the width of the ring electrode as measured along the longitudinal direction of the lead may vary about the perimeter of the lead.

The uneven width of the electrode may bias a stimulation field in a particular direction, e.g., a radial or transverse direction relative to the longitudinal axis of the lead. For example, rather than distributing equally about the perimeter of the lead, as would typically occur when stimulation is delivered via a ring electrode with a substantially even width about the perimeter of the lead, the stimulation field may be biased toward the portion or "side" of the lead body where the electrode has an increased surface area. Electrodes with an uneven width, referred to herein as biased electrodes, may be useful for controlling the direction of propagation of the stimulation field in order to, for example, avoid phrenic nerve stimulation during LV pacing or neck muscle stimulation during vagal neurostimulation.

In one embodiment, an implantable medical lead comprises a lead body insulation and an electrode, wherein a width of the electrode as measured along a longitudinal direction of the lead varies about a perimeter of the lead.

In another embodiment, a system comprises an implantable medical lead, wherein the lead comprises a lead body insulation and an electrode, wherein a width of the electrode as measured along a longitudinal direction of the lead varies about a perimeter of the lead. The system further comprises a medical device that delivers electrical stimulation via the electrode.

In yet another embodiment, a method of implanting an implantable medical lead comprises inserting the lead into a patient. The lead includes lead body insulation, and an electrode positioned on the perimeter of lead body insulation, wherein a width of the electrode as measured along a longitudinal direction of the lead varies about a perimeter of the lead. The method of implanting the implantable medical lead further comprises visualizing an orientation of the lead within the patient; adjusting the orientation of the lead based on the visualization; and delivering therapy to the patient using the electrode.

In another embodiment, a method of manufacturing an implantable medical lead comprises forming a lead body with at least one conductor; and coupling an electrode to the conductor. A width of the electrode as measured along a longitudinal direction of the lead varies about a perimeter of the lead after coupling the electrode to the conductor.

A method comprises implanting an electrical stimulation lead within a patient. The lead comprises a lead body, and an electrode, wherein a width of the electrode as measured along a longitudinal direction of the lead varies about a perimeter of the lead. The method further comprises delivering stimulation therapy to a tissue within the patient using the electrode.

The details of one or more embodiments are set forth in the accompanying drawings and the description below. Other features, objects, and benefits of the present disclosure will be apparent from the description and drawings, and from the claims.

DETAILED DESCRIPTION

In general, the present disclosure is directed toward controlling the direction of propagation of a stimulation field. An implantable medical lead may include at least one biased ring electrode. A width of the biased ring electrode in a longitudinal direction of the lead varies about the perimeter of the lead. The biased electrode may aid in directing a stimulation field in a particular transverse or radial direction. For example, rather than distributing equally about the perimeter of the lead, the stimulation field may be biased to the portion or side of the lead where the biased electrode has an increased surface area. Controlling the direction of the stimulation field may be useful, for example, to avoid phrenic nerve stimulation during LV pacing or neck muscle stimulation during vagal neurostimulation.

While the description primarily refers to implantable medical leads and implantable medical devices, such as pacemakers and pacemaker-cardioverter-defibrillators, that deliver stimulation therapy to a patient's heart, the features of the leads described herein are useful in other types of medical device systems, which may include other types of implantable medical leads and implantable medical devices. For example, leads including the features described herein may be used in systems with medical devices that deliver neurostimulation to the vagal nerve. As other examples, leads including the features described herein may be used in systems that deliver other types of neurostimulation therapy (e.g., spinal cord stimulation or deep brain stimulation), stimulation of one or more muscles or muscle groups, stimulation of one or more organs, such as gastric stimulation, stimulation concomitant to gene therapy, and, in general, stimulation of any tissue of a patient.

Furthermore, although described herein as being coupled to IMDs, implantable medical leads of according to the present disclosure may also be percutaneously coupled to an external medical device for deliver of electrical stimulation to target locations within the patient. Additionally, the disclosure is not limited to embodiments that deliver electrical stimulation to a patient, and includes embodiments in which electrical signals or other physiological parameters are sensed via an implantable medical lead with an electrode having an uneven width about the perimeter of the lead.

For example, for effective cardiac pacing, stimulation therapy can be of adequate energy for a given location to cause depolarization of the myocardium. Sensing a physiological parameter of the patient may be used to verify that pacing therapy has captured the heart, i.e., initiated a desired response to the therapy such as, for example, providing pacing, resynchronization, defibrillation and/or cardioversion. Such sensing may include sensing an evoked R-wave or P-wave after delivery of pacing therapy, sensing for the absence of an intrinsic R-wave or P-wave prior to delivering pacing therapy, or detecting a conducted depolarization in an adjacent heart chamber.

These and other physiological parameters may be sensed using electrodes that may be also used to deliver stimulation therapy. For example, a system may sense physiological parameters using the same electrodes used for providing stimulation therapy or electrodes that are not used for stimulation therapy. As with stimulation therapy, selecting which electrode(s) are used for sensing physiological parameters of a patient may alter the signal quality of the sensing techniques. For this reason, sensing techniques may include one or more algorithms to determine the suitability of each electrode or electrode combination in the stimulation therapy system for sensing one or more physiological parameters. Sensing physiological parameters may also be accomplished using electrode or sensors that are separate from the stimulation electrodes, e.g., electrodes capable of delivering stimulation therapy, but not selected to deliver the stimulation therapy that is actually being delivered to the patient.

Accordingly, a biased electrode having an uneven width about the perimeter of the lead may be selected used, for example, for delivery of electrical stimulation, sensing electrical signals, such as an electrocardiogram for the reasons mentioned above, impedance measurements, or uses known for implanted electrodes in the art. A biased electrode can bias the electric field relative to the lead body. For example, allowing pacing of the left ventricle while reducing nerve stimulation such as Phrenic nerve stimulation. Additionally, targeting nerve stimulation such as the vagus nerve while limiting skeletal muscle stimulation is also achieved through use of a biased electrode.

In addition, while the examples shown in the figures include leads coupled at their proximal ends to a stimulation therapy controller, e.g., implantable medical device, located remotely from the electrodes, other configurations are also possible and contemplated. In some examples, a lead comprises a portion of a housing, or a member coupled to a housing, of stimulation generator located proximate to or at the stimulation site, e.g., a microstimulator. In other examples, a lead comprises a member at stimulation site that is wirelessly coupled to an implanted or external stimulation controller or generator. For this reason, as referred to herein, the term of a "lead" includes any structure having one or more stimulation electrodes disposed on its surface.

Figure 1:
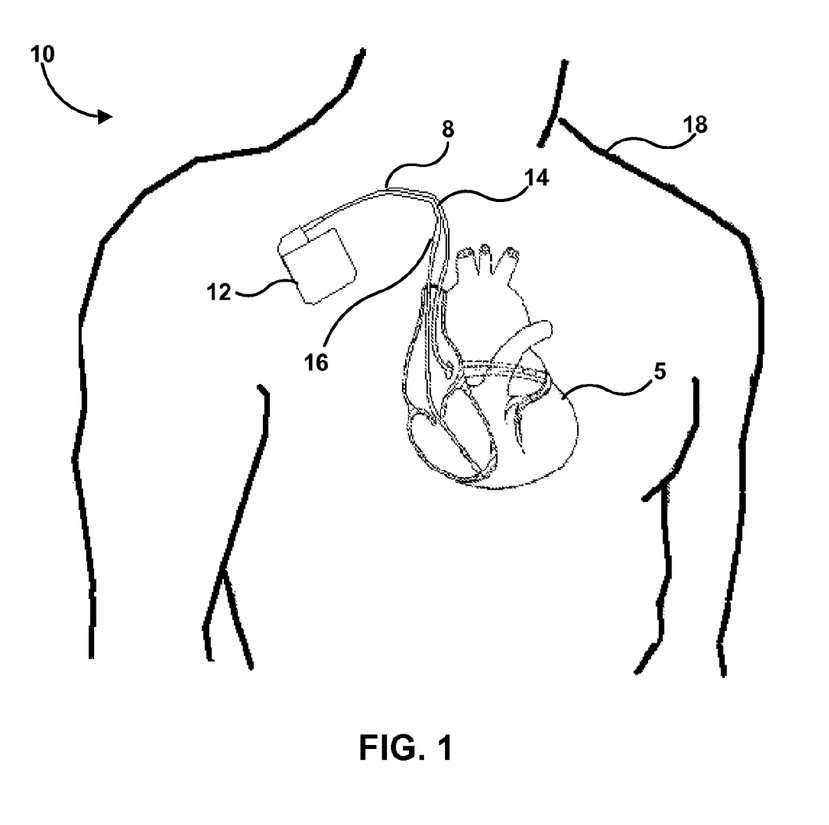
FIG. 1 is a conceptual diagram illustrating an example implantable medical device system.

FIG. 1 is a conceptual diagram illustrating an example implantable medical system 10 comprising implantable medical device (IMD) 12, and implantable medical leads 14, 16 electrically coupled to IMD 12. In the embodiment shown in FIG. 1, system 10 is implanted to deliver stimulation therapy to heart 5 of patient 18. Patient 18 ordinarily, but not necessarily, will be a human patient.

In the embodiment shown in FIG. 1, IMD 12 is an implantable cardiac pacemaker, cardioverter, defibrillator, or pacemaker-cardioverter-defibrillator (PCD), that generates therapeutic electrical stimulation for pacing, cardioversion or defibrillation, which may take the form of pulses or continuous time signals. Leads 14, 16 each include at least one electrode that are each positioned within (e.g., intravenously) or proximate to heart 5 (e.g., an epicedial lead) in order to deliver the therapeutic electrical stimulation from IMD 12 to heart 5. In some embodiments, at least one of leads 14, 16 may provide stimulation to heart 5 without contacting heart 5, e.g., at least one of leads 14, 16 may include a subcutaneous electrode. The electrodes may be disposed proximate to the distal ends of leads 14, 16.

Figure 2A:
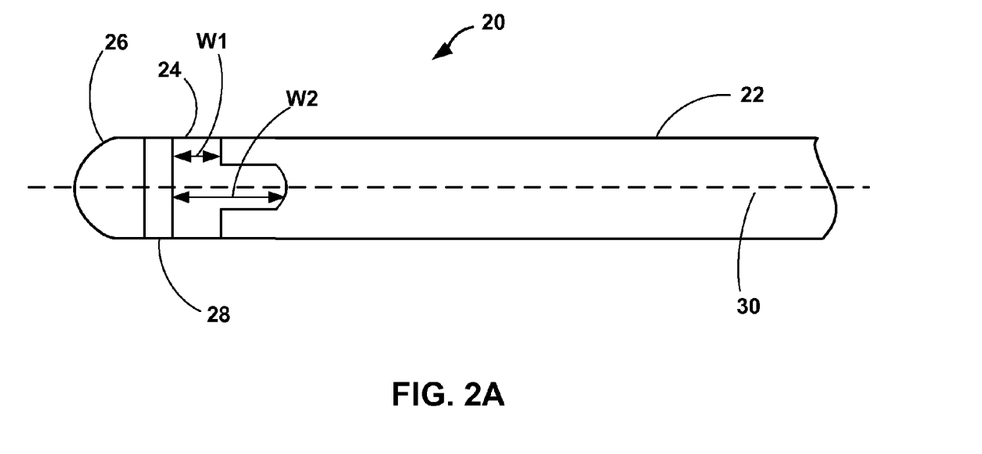
FIG. 2A is a side view of a distal end of an embodiment of an implantable medical lead including a biased ring electrode.

FIG. 2A is a side view of a distal end of an embodiment of a lead 20, which may, for example, correspond to either of leads 14, 16 of FIG. 1. Lead 20 includes a lead body 22 extending from a proximal end (not shown) coupled to an IMD (e.g., IMD 12 of FIG. 1) to a distal end including electrodes 24 and 26. Lead body 22 includes one or more elongated conductors (not shown), one or more electrodes 24, 26, and one or more elongated insulative bodies. The one or more elongated conductors (not shown) covered or surrounded by one or more elongated insulative bodies. The electrodes 24, 26 are coupled to the conductors and are not covered by the insulative body or covering. Allowing electrodes 24, 26 to be exposed to tissue of the patient allows data to be sensed from the tissue and/or therapy delivered to the patient. Exemplary conductors such as cabled conductors or wires can comprise platinum, platinum alloys, titanium, titanium alloys, tantalum, tantalum alloys, cobalt alloys (e.g. MP35N, a nickel-cobalt alloy etc.), copper alloys, silver alloys, gold, silver, stainless steel, magnesium-nickel alloys or other suitable materials. Lead body 22 may be sized based on a target stimulation site within a patient (e.g., patient 18 of FIG. 1) and a path through the patient that lead 20 can traverse in order to place electrodes 24 and 26 at the target stimulation site. Electrodes 24 and 26 may also be sized based on the size of lead 20 and a target stimulation site within the patient.

Lead body 22 along with electrodes 24 and 26 may be, for example, sized to pass through and/or fit in the coronary sinus or a small and/or large coronary vein. Accordingly, lead 20 may correspond to left-ventricular (LV) lead 14 illustrated in FIG. 1, and be used for LV pacing and/or sensing. As another example, for vagal stimulation therapy lead body 22 and electrodes 24 and 26 may be sized to fit within the internal jugular vein of a patient. Lead 20 may also include a monolithic controlled release device (MCRD) 28 containing a steroid. In the embodiment illustrated in FIG. 2A, MCRD 28 is positioned between electrodes 24 and 26.

In the illustrated embodiment, electrode 26 is a tip electrode located at the distal tip of lead 20. In some embodiments, electrode 26 may be formed to provide fixation for lead 20, e.g., may be formed as a helix or screw-like electrode for fixation within tissue of the patient. Electrode 26 may be porous or otherwise allow passage of a steroid or other material from MCRD 28 to patient tissue.

In some embodiments, electrode 26 may be a ring electrode with a substantially circular cross-section. In other embodiments, electrode 26 may comprise a plurality of segmented or partial ring electrodes, each of the electrode segments extending along an arc less than 360 degrees (e.g., 90-120 degrees) about the circumference or perimeter of lead 20. Segmented or partial ring electrodes may be useful for providing an electrical stimulation field in a particular propagation direction and/or targeting a particular stimulation site by selective activation of electrodes most proximate to the site, or facing in the desired propagation direction.

As shown in FIG. 2A, electrode 24 is a biased ring electrode. The width of biased ring electrode 24 as measured along the longitudinal axis 30 of the lead 20, i.e., a longitudinal direction, varies about the perimeter, e.g., circumference, of the lead 20. More specifically, the width of ring electrode 24 varies around a circumference of lead 20 such that the surface area of ring electrode 24 is greater on one side or portion of lead 20, e.g., within a particular radial section of lead 20.

In the embodiment illustrated in FIG. 2A, a first radial portion of ring electrode 24 has a width W1, and a second radial portion of ring electrode 24 has a width W2. Width W2 is greater than width W1 such that the portion, e.g., radial section, of electrode 24 with increased width W2 forms a protrusion in the direction of longitudinal axis 30. In some embodiments, W2 is about 2 mm to 20 mm larger than width W1. As another example, W2 may be about 1 to 2000 percent larger than width W1. In yet another embodiment, W2 may be about 25 percent larger than width W1. In yet another embodiment, W2 may be about 30 percent larger than width W1. In yet another embodiment, W2 may be about 40 percent larger than width W1. In yet another embodiment, W2 may be about 50 percent larger than width W1. In yet another embodiment, W2 may be about 60 percent larger than width W1. In yet another embodiment, W2 may be about 70 percent larger than width W1. In yet another embodiment, W2 may be about 80 percent larger than width W1. In yet another embodiment, W2 may be about 90 percent larger than width W1. In yet another embodiment, W2 may be about 100 percent larger than width W1. In yet another embodiment, W2 may be about 200 percent larger than width W1. In yet another embodiment, W2 may be about 300 percent larger than width W1. In yet another embodiment, W2 may be about 400 percent larger than width W1. In yet another embodiment, W2 may be about 500 percent larger than width W1. In yet another embodiment, W2 may be about 600 percent larger than width W1. In yet another embodiment, W2 may be about 700 percent larger than width W1. In yet another embodiment, W2 may be about 800 percent larger than width W1. In yet another embodiment, W2 may be about 900 percent larger than width W1. In yet another embodiment, W2 may be about 1000 percent larger than width W1. The relationship between widths W1 and W2 may be configured to control the direction of propagation of a stimulation field generated using biased electrode 24.

When biased electrode 24 is activated (i.e., as a cathode or an anode) to deliver stimulation, the resulting stimulation field is biased towards the side or radial portion of biased electrode 24 having a greater surface area, e.g., propagates a greater distance outward from the lead body in a radial, transverse or cross-sectional direction. In contrast, a stimulation field from a ring electrode having a substantially constant width about the perimeter of a lead body is substantially equally distributed about the perimeter of the lead 20, i.e., propagates a substantially constant transverse or radial distance from the lead.

A biased ring electrode can be useful in directing a stimulation field toward a target tissue site and/or away from an undesirable tissue site. As one example, a directional stimulation field may be particularly useful in left ventricle (LV) pacing applications. The biased ring electrode may allow the field to be directed toward the myocardium and away from the phrenic nerve.

As another example, a biased ring electrode may be useful in stimulation of the vagus nerve. Stimulation of the vagus nerve may be performed to, for example, decrease or otherwise regulate heart rate. The vagus nerve is positioned proximate to muscles of the neck, which may inadvertently be stimulated along with the vagus nerve. Controlling the direction of the stimulation field may aid in preventing stimulation of the neck muscles.

As another example, a directional electrical field may be useful in atrial stimulation, where it may be desirable to avoid stimulating specific ischemic tissue regions. In general, a biased ring electrode may be beneficial in any application where controlling the direction of propagation of the stimulation field, e.g., in a transverse, radial or cross-sectional direction, is desirable.

Electrode 24 may be activated as a cathode or anode, with electrode 26 or another electrode, e.g., an electrode located on a housing of an IMD, such as IMD 12, activated with the opposite polarity. Furthermore, although electrode 24 has an uneven width in the illustrated embodiment, either or both of electrodes 24 and 26 may have an uneven width in various embodiments. Accordingly, in some embodiments, a tip electrode may be a biased electrode and, in various embodiments, a biased electrode may act as either an anode or cathode for delivery of stimulation to a patient.

Additionally, the disclosure is not limited to embodiments in which the biased electrode has the shape or form illustrated by electrode 24 in FIG. 2A. A biased electrode may include a portion, e.g., radial section, that forms a protrusion in the direction of longitudinal axis 30, as illustrated by electrode 24 in FIG. 2A. The remainder of the biased electrode may, but need not necessarily, take the form of a ring electrode with a substantially constant width, as illustrated by electrode 24 in FIG. 2A. However, in other embodiments, a biased electrode may have any shape or form. For example, one or both of the edges of the electrode may define a regular, irregular, or random, curvilinear or geometric line around the perimeter of lead body, such that the width of the electrode in the direction of longitudinal axis 30 varies around the perimeter.

At least a portion of lead 20, such as electrodes 24 and 26 or a separate marker loaded in or formed on lead body 22, may include a radio-opaque material that is detectable by imaging techniques, such as fluoroscopic imaging or x-ray imaging. For example, electrodes 24 and 26 may be made of platinum or another material detectable by imaging techniques. This feature may be helpful for maneuvering lead 20 relative to a target site within the body. Radio-opaque markers, as well as other types of markers, such as other types of radiographic and/or visible markers, may also be employed to assist a clinician during the introduction and withdrawal of lead 20 from a patient. Markers identifying a portion or side of a lead in which an electrode has a greater width (and, accordingly, greater surface area) may be particularly helpful. Since the electrodes rotate with the lead body, a clinician may rotate the lead and the electric field to stimulate a desire tissue, i.e., rotate the lead such that the portion with greater electrode surface area faces target tissue and/or is directed away from tissue to which delivery of stimulation is undesirable. Markers may help guide the rotation to control the direction of propagation of the stimulation field once the lead is implanted.

In the embodiment illustrated in FIG. 2A, electrodes 24 and 26 may be coupled to an IMD (e.g., IMD 12 of FIG. 1) using an industry standard-1 (IS-1) connector, which allows the connection of up to two independently activatable channels. More specifically, electrical conductors (not shown) may couple electrodes 24 and 26 to an IMD (e.g., IMD 12 of FIG. 1) via an IS-1 connector. Some commercially available IMDs are configured according to the IS-1 standard. An IS-1 compatible lead may be easily coupled to these commercially available devices. In other embodiments, lead 20 may include any configuration, type, and number of electrodes 24 and 26 and is not limited to the embodiment illustrated in FIG. 2A.

Figure 2B:
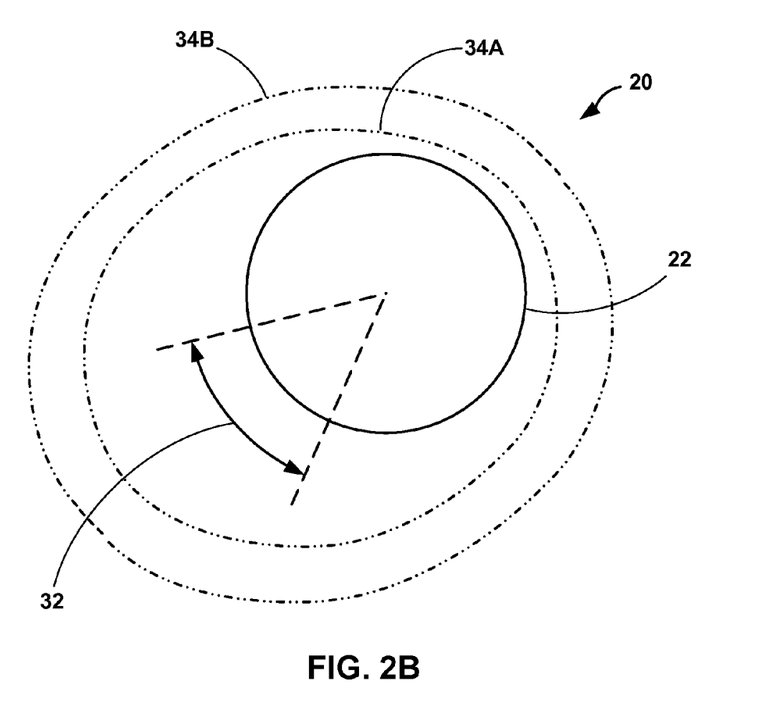
FIG. 2B is a cross-sectional view of a distal end of the implantable medical lead of FIG. 2A.

FIG. 2B is a cross-sectional view of a distal end of implantable medical lead 20 illustrating radial section 32. Radial section 32 corresponds to the portion of electrode 24 with increased width W2 in the direction of longitudinal axis 30 as illustrated in FIG. 2A. Radial section 32 extends around a portion of the perimeter of lead 20. Due to the increased width W2 of electrode 24 at radial section 32, electrode 24 also has an increased surface area at radial section 32. When biased electrode 24 is activated (i.e., as a cathode or an anode) to deliver stimulation, the resulting stimulation field is biased towards radial section 32 of biased electrode 24, i.e., the resulting stimulation field propagates a greater distance outward from lead 20 in a radial, transverse or cross-sectional direction. Outlines 34A and 34B represent the outer boundaries of example stimulation fields that may be generated when biased electrode 24 is activated to deliver stimulation and illustrate how the stimulation fields propagate a greater distance outward from lead 20 proximate to radial section 32 compared to the other portions of the perimeter of lead 20. The actual stimulation field is dependent not only on the shape of biased electrode 24, but also other factors such as the amplitude of stimulation therapy, the location and configuration of addition electrodes such as electrode 26, as well as the impedance of patient tissue or other substances adjacent to the stimulation field. As referred to herein, an amplitude of stimulation therapy may be characterized as a magnitude of a time varying waveform. For example, an amplitude of stimulation therapy may be measured in terms of voltage (volts), current (ampere), or electric field (volts/meter). Typically, amplitude is expressed in terms of a peak, peak to peak, or root mean squared (rms) value.

Figure 3:
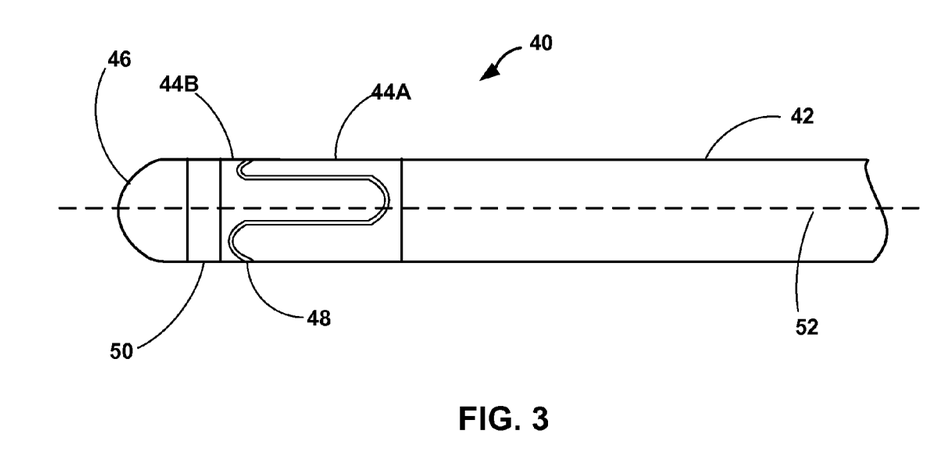
FIG. 3 is a side view of a distal end of another embodiment of an implantable medical lead including two biased ring electrodes that are complimentary along an interface between the two electrodes.

FIG. 3 is a side view of a distal end of another embodiment of an implantable medical lead 40. Lead 40 is similar to lead 20 of FIGS. 2A and 2B but, as described in further detail below, includes three electrodes 44A, 44B, and 46. Lead 40 includes a lead body 42 that extends from a proximal end (not shown) coupled to an IMD (e.g., IMD 12 of FIG. 1) to a distal end that includes electrodes 44A, 44B, and 46. Electrode 46 may take any of the forms described above with respect to electrode 26 and FIG. 2A. Furthermore, lead 40 may include an MCRD 50 that may substantially similar to and provides substantially the same functionality as MCRD 28 described above with respect to FIG. 2A.

In the embodiment illustrated in FIG. 3, lead body 42 includes two biased ring electrodes 44A and 44B. A width of each of electrode 44A and 44B as measured along the direction of longitudinal axis 52 of the lead body 42, i.e., a longitudinal direction, varies around a perimeter of lead 40. In the embodiment illustrated in FIG. 3, electrodes 44A and 44B are substantially complimentary. In particular, as shown in FIG. 3, when the width of one of electrodes 44A and 44B in the longitudinal direction changes, the width of the other of electrodes 44A and 44B also changes with a substantially equal but opposite magnitude. Thus, in the embodiment illustrated in FIG. 3, the sum of the widths of electrodes 44A and 44B may be substantially about the same at any circumferential position of lead 40. Substantially about the same, in one embodiment, means that the sum of the widths of electrodes 44A and 44B are within 20 percent of one another. Electrodes 44A and 44B are also complimentary in the sense that the lines (curvilinear in the illustrated example) around the perimeter of lead 40 formed by the adjacent edges of the electrodes, e.g., the edges where electrodes 44A and 44B interface, are substantially similar. Insulative material 48 separates electrodes 44A and 44B to electrically isolate electrodes 44A and 44B. For example, insulative material 48 may comprise polyurethane, silicone, and fluoropolymers such as tetrafluroethylene (ETFE), polytetrafluroethylene (PTFE), and/or expanded PTFE (i.e. porous ePTFE, nonporous ePTFE).

The surface area and shape of each of electrodes 44A, 44B, and 46 may be selected based on the desired stimulation field. For example, the surface area and shape of each of electrodes 44A, 44B, and 46 may be selected to aid in selectively exciting a tissue based on the geometrical proximity to lead 40 and/or the field gradient to which the target tissue responds. Any of electrodes 44A, 44B, and 46 may be configured as a cathode or an anode to aid in creating the desired stimulation field. As one example, electrode 44A may be configured as an anode, and electrode 44B may be configured as a cathode to create a desired stimulation field. As another example, electrode 46 may be activated as an anode or cathode, and one of electrodes 44A and 44B may be activated with the opposite polarity. Which of electrodes 44A and 44B is selected may be based on a desired direction of propagation or shape of the stimulation field.

Figure 4:
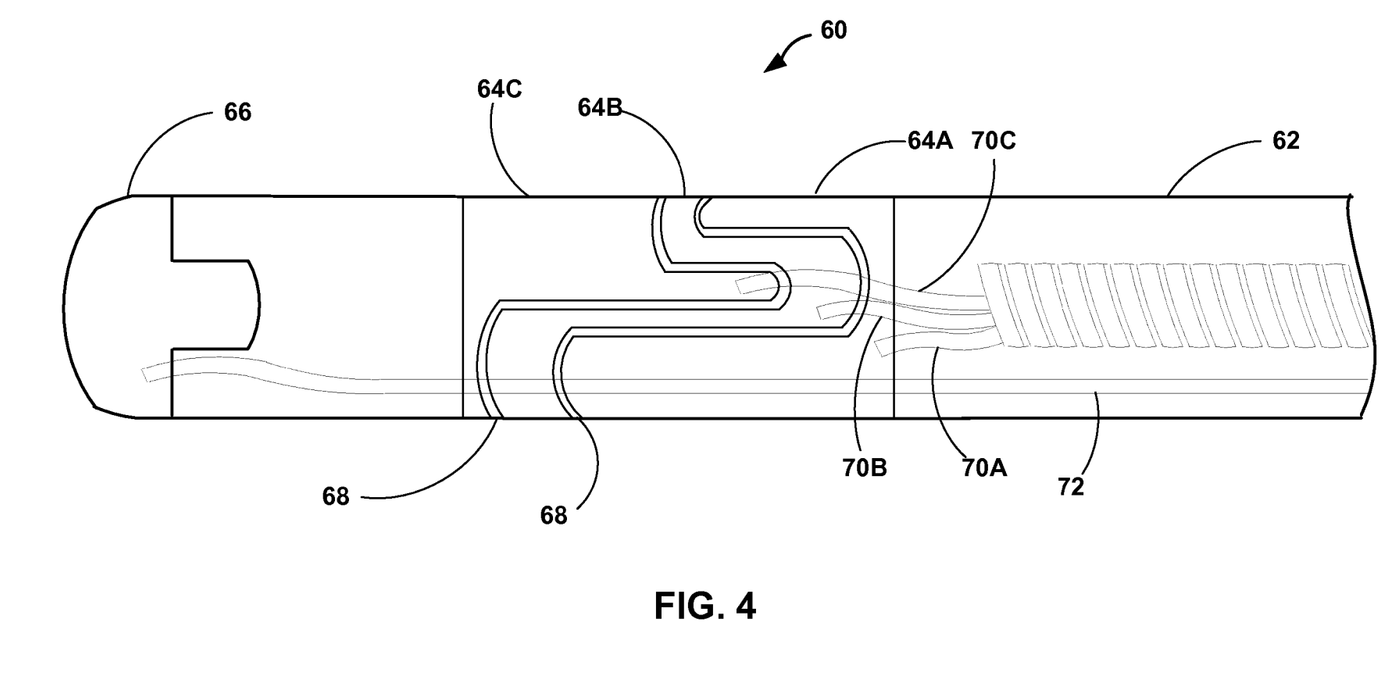
FIG. 4 is a side view of a distal end of another embodiment of an implantable medical lead including three biased ring electrodes and illustrating electrical conductors within the lead body.

FIG. 4 is a side view of a distal end of an embodiment of an implantable medical lead 60. Lead 60 includes a lead body 62 that extends from a proximal end (not shown) coupled to an IMD (e.g., IMD 12 of FIG. 1) to a distal end that includes electrodes 64A-64C and 66. Lead body 62 may be sized to fit in a small and/or large coronary vein. Accordingly, electrodes 64A-64C and 66 may also be sized based on the size of lead body 62 and a target stimulation site within a patient (e.g., patient 18 of FIG. 1). In other embodiments, lead 60 may include any configuration, type, and number of electrodes 64A-64C and 66 and is not limited to the embodiment illustrated in FIG. 4.

In the embodiment illustrated in FIG. 4, lead 60 includes biased ring electrode 66 at its distal tip and three biased ring electrodes 64A-64C axially displaced from biased ring electrode 66. A width of each of electrode 64A-64C and 66 in the longitudinal direction, i.e., in the direction along a longitudinal axis (not shown) of lead 60, varies around a circumference or perimeter of lead 60. For example, electrode 64 includes an increased width and surface area at one portion of the circumference of lead 60.

Electrodes 64A and 64B are substantially complimentary. For example, when one of electrodes 64A and 64B changes shape along the interface between electrodes 64A and 64B, the other of electrodes 64A and 64B also changes shape in an opposite direction but with an equal magnitude. Similarly, electrodes 64B and 64C are also substantially complimentary. In the embodiment illustrated in FIG. 4, the sum of the widths of electrodes 64A-64C may be substantially the same at any circumferential position of lead 60. Insulative material 68 separates electrodes 64A and 64B and also separates electrodes 64B and 64C. Insulative material 68 may aid in electrically isolating electrodes 64A-64C. For example, insulative material 68 may comprise polyurethane, silicone, and fluoropolymers such as tetrafluroethylene (ETFE), polytetrafluroethylene (PTFE), and/or expanded PTFE (i.e. porous ePTFE, nonporous ePTFE).

The surface area and shape of each of electrodes 64A-64C and 66 may be selected based on the desired stimulation field. For example, the surface area and shape of each of electrodes 64A-64C and 66 may be selected to target a tissue based on the geometrical proximity to lead 60 and/or the field gradient to which the target tissue responds. Any of electrodes 64A-64C and 66 may be configured as a cathode or an anode to aid in creating the desired stimulation field. As one example, electrodes 64A and 64C may be configured as anodes and electrode 64B may be configured as a cathode to create a desired stimulation field. As another example, electrode 66 may be activated as an anode or cathode, and one of electrodes 64A-64C may be activated with the opposite polarity to create a desired stimulation field, with the selection of which of electrodes 64A-64C is activated being based on the desired stimulation field, the orientation of lead 60 and electrodes 64A-64C relative to target patient tissue for stimulation or tissue to be avoided, or the like.

Lead 60 also includes conductors 70A-70C and 72 electrically coupled to electrodes 64A-64C and 66, respectively. In the illustrated embodiment, conductors 70A-70C are coiled along the length of lead body 62, and conductor 72 lays axial to conductors 70A-70C. Although not illustrated in FIG. 4, conductor 72 may also be coiled, and may or may not be braided with conductors 70A-70C. In the embodiment illustrated in FIG. 4, each of conductors 70A-70C and 72 is electrically coupled to a single one of electrodes 64A-64C and 66, respectively. In this manner, each of electrodes 64A-64C and 66 may be independently activated. Electrodes 64A-64C and 66 may be coupled to an IMD (e.g., IMD 12 of FIG. 1) using, for example, an industry standard-4 (IS-4), which allows the connection of up to four independently activatable channels. More specifically, conductors 70A-70C and 72 may couple electrodes 64A-64C and 66 to an IMD (e.g., IMD 12 of FIG. 1) via an IS-4 connector.

The configuration, type, and number of electrical conductors 70A-70C and 72 is not limited to the embodiment illustrated in FIG. 4 and, in other embodiments, lead 60 may include any configuration, type, and number of conductors. As one example, in some embodiments, each of conductors 70A-70C and 72 may be coiled conductors. Additionally or alternatively, one conductor may be electrically coupled to two or more electrodes. Additionally, each of leads 12, 14, 20 and 40 may include conductors to electrically couple its electrodes at the distal end of its lead body to an IMD (e.g., IMD 12 of FIG. 1) coupled to the proximal end of its lead body. In another embodiment, a lead including multiple electrodes may include a multiplexer or other switching device such that the lead body may include fewer conductors than electrodes while allowing each of the electrodes to be individually selectable.

Figure 5:
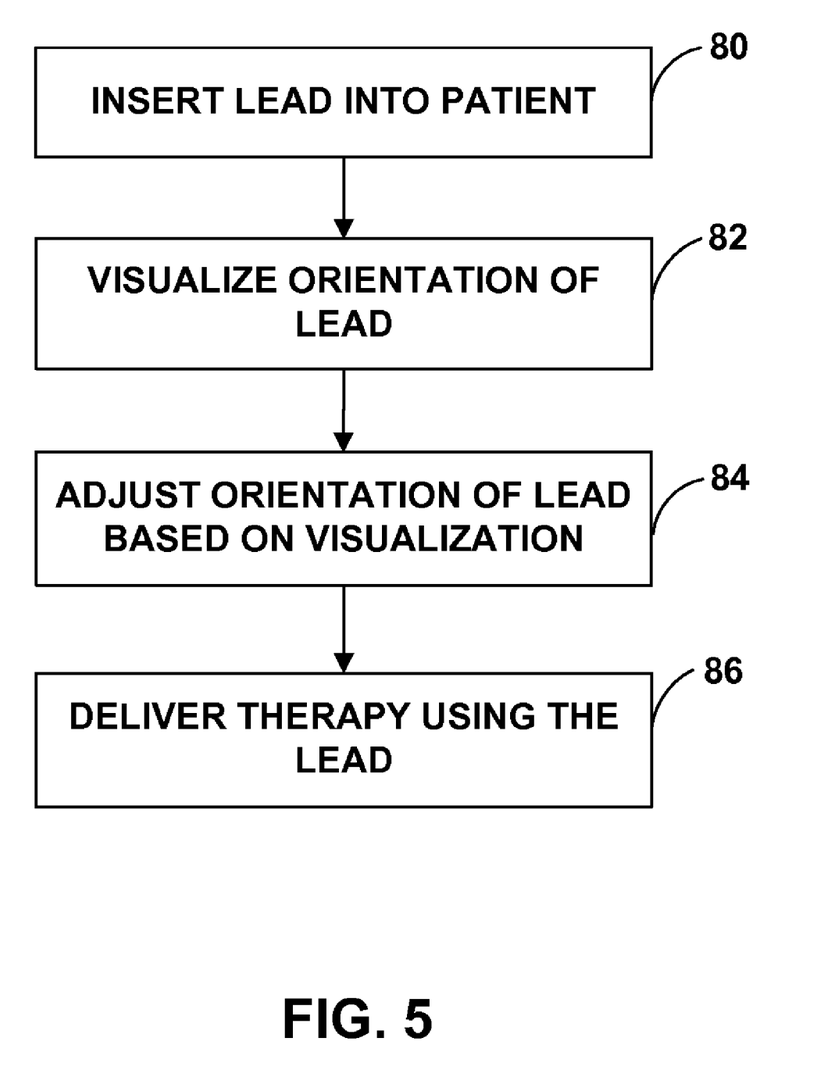
FIG. 5 is a flowchart illustrating a method of using an implantable medical lead with a biased electrode.

FIG. 5 is a flowchart illustrating a method of using an implantable medical lead with a biased electrode. A lead comprising a biased electrode is inserted into a patient (80) and its distal end is guided to a target tissue site. The target tissue site may be, for example, the myocardium of the heart, near the phrenic nerve, the vagus nerve, or any other location where controlling the direction of propagation of the stimulation field is desirable.

Once the distal end of the lead is positioned at the target tissue site, an orientation of the lead is visualized (82), and the orientation is adjusted based on the visualization (84). As described previously, radio-opaque markers, as well as other types of markers, such as other types of radiographic and/or visible markers, may also be employed to assist a clinician during the introduction and withdrawal of a lead comprising a biased electrode from a patient. Markers identifying a portion or side of a lead in which an electrode has a greater width (and, accordingly, greater surface area) may be particularly helpful. Since the electrodes rotate with the lead body, a clinician may rotate the lead and the electric field to stimulate a desire tissue, i.e., rotate the lead such that the portion with greater electrode surface area faces target tissue and/or is directed away from tissue to which delivery of stimulation is undesirable. Markers may help guide the rotation to control the direction of propagation of the stimulation field once the lead is implanted.

Once the lead is properly orientated, therapy is delivered to the patient using one or more electrodes of the lead (86). For example, a medical device coupled to the implantable medical lead may activate the electrode to deliver therapy to the patient. In some embodiments, the medical device may deliver one or more electrical test signals to the patient to verify that the lead is properly orientated prior to initiating therapy delivery.

Figure 6:
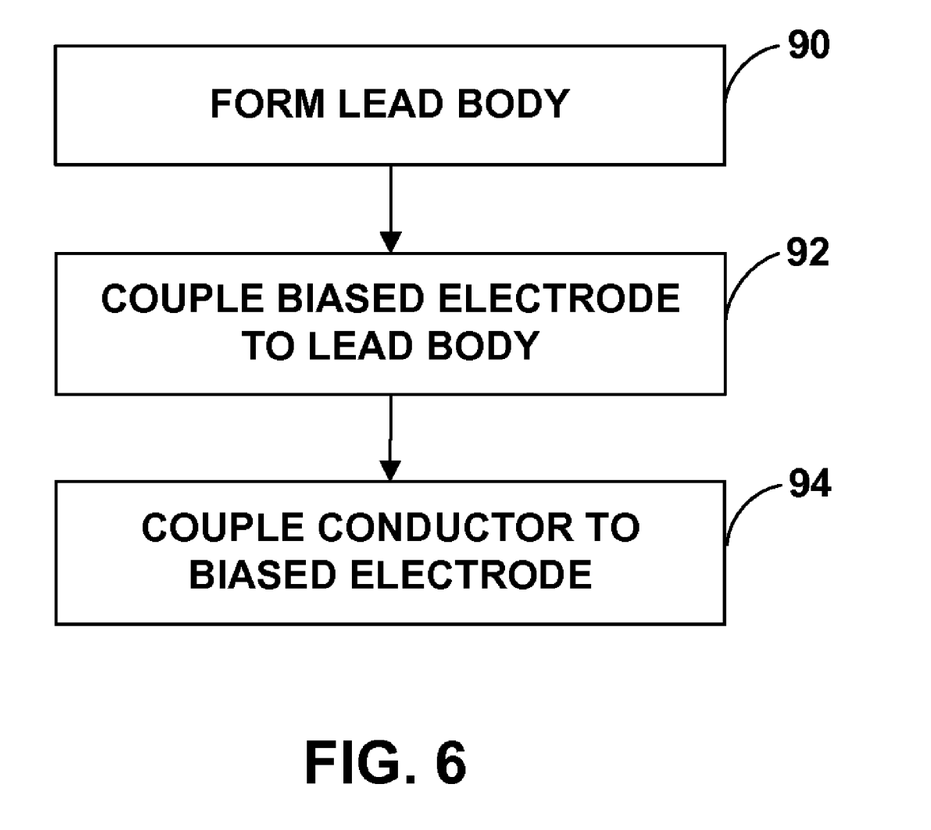
FIG. 6 is a flowchart illustrating a method of manufacturing an implantable medical lead with a biased electrode.

FIG. 6 is a flowchart illustrating a method of manufacturing an implantable medical lead with a biased electrode. The method comprises forming a lead body (90) and coupling the biased electrode to the lead body (92). In some embodiments, the lead body is formed using extrusion, and the biased electrode may be positioned on the lead body such that an outer surface of the biased electrode is substantially flush with an outer surface of the lead body. In other embodiments, the biased electrode is placed in a mold and an electrically insulating material is injected into the mold to create the lead body. In this manner, the biased electrode may be integral to the lead body.

Additionally, an electrical conductor is coupled to the biased electrode (94). The conductor extends from a proximal end of the lead body to the biased electrode and allows a medical device coupled to the proximal end of the lead body to deliver an electrical signal to the biased electrode. In one embodiment, the conductor is placed within a lead body coupled to the biased electrode. A distal end of the conductor may be welded or otherwise coupled to the biased electrode. In some embodiments, the electrically insulating lead body includes an aperture that allows the conductor and biased electrode to make electrical contact. In embodiments in which the lead body is injection molded, the conductor may be electrically coupled to the biased electrode and positioned within the mold prior to the injection of the electrically insulating material. As this example illustrates, in some embodiments, the conductor may be coupled to the biased electrode before the lead body is formed and/or before the biased electrode is coupled to the lead body.

Various examples have been described. However, one of ordinary skill in the art will appreciate that various modifications may be made to the described examples. For example, although leads in which biased electrodes are ring electrodes or otherwise extend substantially completely around the perimeter of the lead have been described herein, a biased electrode may be discontinuous or otherwise extend only partially around the perimeter of a lead, but nevertheless have a width that varies in the longitudinal direction around the perimeter of the lead. As another example, leads used in conjunction with the techniques described herein may include fixation mechanisms, such as tines that passively secure a lead in an implanted position or a helix located at a distal end of the lead that required rotation of the lead during implantation to secure the helix to a body tissue. Further, although depicted herein as being located at a distal end of a lead body, in other examples a biased electrode may be located on any portion of a lead body. These and other examples are within the scope of the following claims.

The invention claimed is:

1. An implantable medical lead comprising:
a lead insulative body; and
electrodes along a perimeter of the insulative body, wherein widths of the electrodes as measured along a longitudinal direction of the lead vary about a perimeter of the lead; and
wherein the electrodes comprise a first electrode and a second electrode axially displaced along a length of the insulative body from the first electrode; and
wherein a width of the second electrode varies in the longitudinal direction about the perimeter of the lead; and
wherein a sum of the width of the first electrode and the width of the second electrode is the same around the perimeter of the lead.

2. The lead of claim 1, wherein the first and second electrodes are complimentary along an interface between the first and second electrodes.

3. The lead of claim 2, further comprising an insulative material between the first and second electrodes.

4. A system comprising:
an implantable medical lead, wherein the lead comprises:
a lead body; and
electrodes, wherein widths of the electrodes as measured along a longitudinal direction of the lead vary about a perimeter of the lead; and
a medical device that delivers electrical stimulation via the electrodes; and
wherein the electrodes comprise a first electrode and a second electrode axially displaced along a length of the lead from the first electrode; and
wherein the second electrode comprises a ring electrode, wherein the width of the second electrode varies about the perimeter of the lead; and
wherein a sum of the width of the first electrode and the width of the second electrode is substantially the same around a circumference of the lead.

5. The system of claim 4, wherein the medical device is configured to selectively activate at least one of the first electrode and the second electrode to control a direction of propagation of a stimulation field emanating from the selected electrodes.

6. The system of claim 4, wherein the first and second electrodes are complimentary along an interface between the first and second electrodes.

7. The lead of claim 6, further comprising an insulative material between the first and second electrodes.

8. The system of claim 6, further comprising a third electrode, wherein a width of the third electrode varies about the perimeter of the lead, and wherein the second and third electrodes are complimentary along an interface between the second and third electrodes.

9. The system of claim 8, wherein a sum of the width of the first electrode, the width of the second electrode, and the width of the third electrode are substantially the same about the perimeter of the lead.

10. The system of claim 8, further comprising an insulative material between the first and second electrodes and the second and third electrodes.

11. The system of claim 8, further comprising a fourth electrode positioned at a distal tip of the lead.

12. The system of claim 4, wherein the medical device comprises an implantable medical device.

13. The system of claim 4, wherein the medical device comprises a cardiac stimulator.

* * * * *